United States Patent [19]
Wilk

[11] Patent Number: 5,246,424
[45] Date of Patent: Sep. 21, 1993

[54] DEVICE AND METHOD FOR USE IN OBTAINING ACCESS TO AN INTERNAL BODY ORGAN

[76] Inventor: Peter J. Wilk, 185 W. End Ave., New York, N.Y. 10023

[21] Appl. No.: 893,991

[22] Filed: Jun. 5, 1992

Related U.S. Application Data

[63] Continuation-in-part of Ser. No. 851,097, Mar. 13, 1992, Pat. No. 5,230,705.

[51] Int. Cl.⁵ .................................... A61M 25/01
[52] U.S. Cl. ........................... 604/164; 604/158
[58] Field of Search ............. 606/119, 191, 193, 198; 604/104, 158, 164, 171, 280–282

[56] References Cited

U.S. PATENT DOCUMENTS

| | | | |
|---|---|---|---|
| 250,154 | 11/1881 | Master | 602/63 |
| 3,788,318 | 1/1974 | Kim et al. | 606/198 X |
| 4,018,230 | 4/1977 | Ochiai et al. | 606/193 |
| 4,411,655 | 10/1983 | Schreck | 604/165 |
| 4,449,532 | 5/1984 | Storz . | |
| 4,480,642 | 11/1984 | Stoy et al. | 606/193 |
| 4,581,019 | 4/1986 | Curelaru et al. . | |
| 4,716,901 | 1/1988 | Jackson et al. . | |
| 4,759,748 | 7/1988 | Reed | 604/95 |
| 4,827,925 | 5/1989 | Vilasi | 128/207.14 |
| 4,850,975 | 7/1989 | Furukawa . | |
| 4,862,891 | 5/1989 | Smith . | |
| 4,899,729 | 2/1990 | Gill et al. | 128/3 |
| 4,919,133 | 4/1990 | Chiang . | |
| 4,994,070 | 2/1991 | Waters . | |
| 5,057,083 | 10/1991 | Gellman . | |
| 5,112,308 | 5/1992 | Olsen et al. . | |
| 5,139,477 | 8/1992 | Peters | 602/26 |
| 5,139,486 | 8/1992 | Moss | 604/164 |
| 5,139,511 | 8/1992 | Gill et al. | 606/198 |

*Primary Examiner*—C. Fred Rosenbaum
*Assistant Examiner*—Corrine Maglione
*Attorney, Agent, or Firm*—R. Neil Sudol; Henry D. Coleman

[57] ABSTRACT

A dilating device for use in obtaining access to a body organ of a patient comprises, in accordance with the present invention, a plurality of elongate rigid members extending substantially parallel to one another, and an elastic membrane connected to the rigid members for defining a transversely expandable longitudinally extending channel. The rigid members take the form of elongate, substantially cylindrical or conical segments. A needle is inserted through the channel defined by the membrane and the rigid segments. Alternatively, the dilating device is inserted through the needle. Upon expansion of the dilating device, an instrument such as a catheter or endoscope is inserted to implement a surgical or diagnostic procedure.

13 Claims, 3 Drawing Sheets

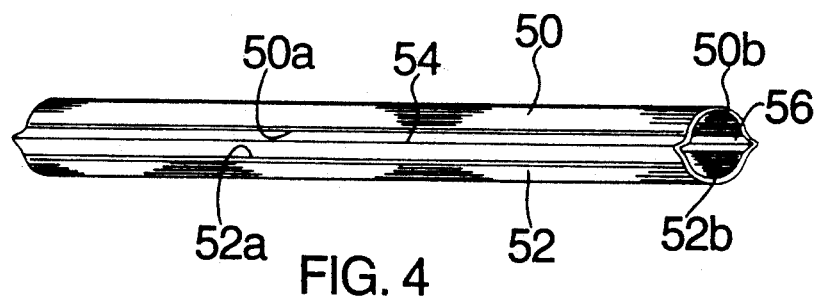
FIG. 4
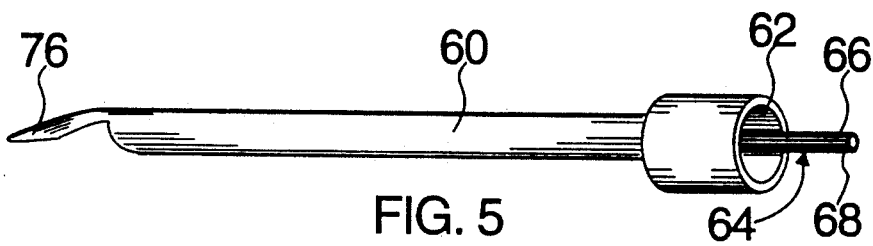
FIG. 5
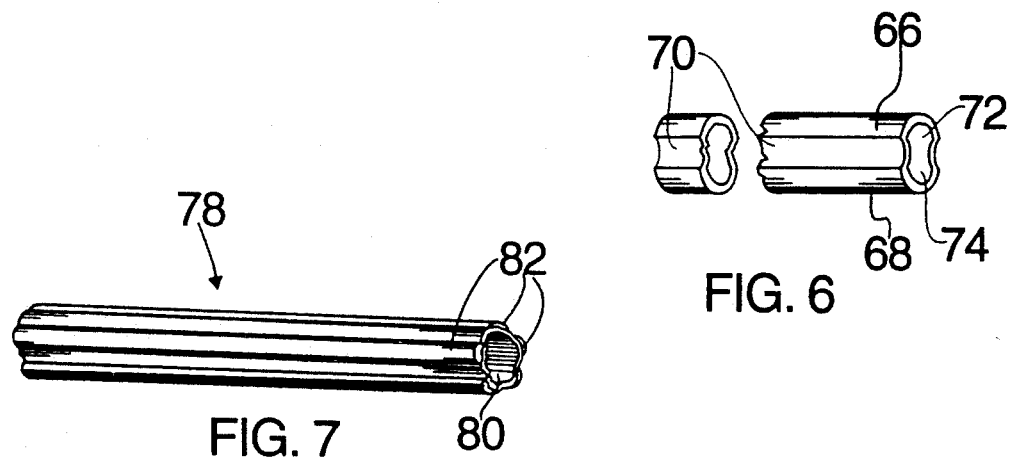
FIG. 6
FIG. 7
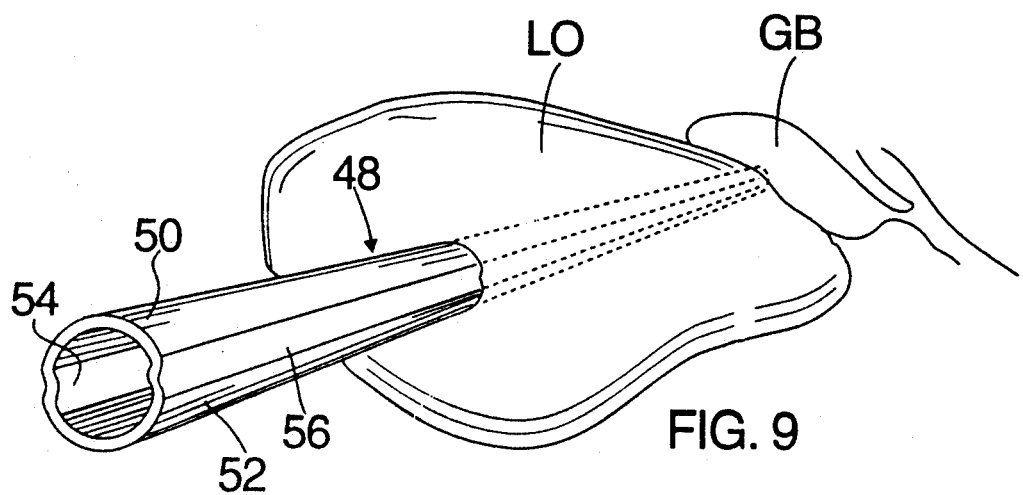
FIG. 9

DEVICE AND METHOD FOR USE IN OBTAINING ACCESS TO AN INTERNAL BODY ORGAN

CROSS-REFERENCE TO A RELATED APPLICATION

This application is a continuation-in-part of commonly owned application Ser. No. 851,097 filed Mar. 13, 1992, now U.S. Pat. No. 5,230,705.

FIELD OF THE INVENTION

This invention relates to a device and an associated method for use in obtaining access to an internal organ of a patient.

The internal organ may be a blood vessel. In that event, this invention more specifically relates to a device and an associated method for use in obtaining intravenous or intra-arterial access.

The internal organ may alternatively take the form of the liver, the brain, the thalamus, or other organ. In that case, this invention more specifically relates to a device and an associated method for obtaining visual and operative access to an internal portion of an organ.

This invention additionally relates to a catheter and to a method for inserting or deploying a catheter in a vein or artery.

BACKGROUND OF THE INVENTION

A catherization procedure involves the piercing of a vein or artery with a needle carrying a catheter and subsequently sliding the catheter over the needle and into the punctured blood vessel. After the needle is removed from the catheter, an intravenous tube is connected to the catheter for supplying an intravenous fluid to the patient.

Frequently, a large intravenous flow rate is required in situations where the number or sizes of the accessible veins are severely limited. Consequently, large catheters are inserted into relatively small veins, which results in tears in the veins. Catheters inserted into torn veins fall out. This naturally gives rise to a potentially dangerous circumstance.

In one method for inserting a relatively large catheter into a vein, a small catheter is deployed in a selected vein. Upon the removal of the needle used to pierce the vein, a wire is inserted through the catheter. The catheter is then removed. A vein dilating device having a substantially rigid tapered body is gradually inserted into the vein over the wire, thereby expanding the access opening in the vein. The dilator is subsequently removed and replaced with a large diameter catheter. Finally, the wire is withdrawn from the large catheter.

Obtaining access to larger organs such as the liver or the brain for purposes of viewing or operating on an inner part of the organ generally requires cutting open the respective organ. Such an invasive procedure necessarily entails trauma to the patient, extended hospital stays and excessive costs.

OBJECTS OF THE INVENTION

A general object of the present invention is to provide a device and an associated method for use in obtaining access to an internal organ of a patient.

A more specific object of the present invention is to provide a device and an associated method for facilitating visual and operative access to an internal portion of an internal body organ such as the liver, or to another organ such as the gall bladder via the liver.

An additional specific object of the present invention is to provide a device and an associated method for enabling such visual and operative access via an endoscopic instrument.

Another object of the present invention is to provide a method for inserting a relatively large catheter into a vein.

Another, more particular, object of the present invention is to provide such a method which has fewer steps than the above-described wire-facilitated technique.

Another object of the present invention is to provide a device for facilitating the insertion of a relatively large diameter catheter into a vein.

A further particular object of the present invention is to provide such a device which reduces the incidence of torn veins.

Yet another particular object of the present invention is to provide such a device which is easy and inexpensive to manufacture.

Other objects of the present invention will be apparent from the detailed descriptions and drawings included herein.

SUMMARY OF THE INVENTION

A device for use in obtaining access to a body organ of a patient comprises, in accordance with the present invention, a plurality of elongate rigid members extending substantially parallel to one another, and an elastic membrane connected to the rigid members for defining a transversely expandable longitudinally extending channel.

Preferably, the rigid members take the form of elongate, substantially cylindrical or conical segments. The segments each have a pair of longitudinally extending edges, the membrane being connected to the segments along the edges. In a more specific embodiment of the invention, the membrane is one of a plurality of distinct membrane sections each connected to a pair of the segments along respective ones of the edges.

Pursuant to another specific embodiment of the present invention, a needle is inserted through the channel defined by the membrane. Moreover, a catheter surrounding the needle may be inserted therewith into the channel.

According to another feature of the present invention, the device is a dilating device for assisting in the disposition of an intravenous or intra-arterial catheter. Alternatively, the device is a catheter designed to remain in the vein or artery.

According to another feature of the present invention, the device is a dilating device for assisting in the insertion of an endoscopic device at least partially through an internal organ.

A device for use in obtaining access to an internal organ of a patient comprises, in accordance with the present invention, a hollow needle with a longitudinally extending passage and a dilating component disposed in the passage, the dilating component including at least one elongate rigid member and an elastic membrane connected to the rigid member for defining therewith a longitudinally extending transversely expandable channel.

As described above, the rigid member in this combination of a needle and a dilating component is preferably one of a plurality of elongate rigid members extending parallel to one another, the membrane being attached to each of the rigid members. In a specific embodiment of the invention, the rigid members are cylindrical or conical segments.

A method for use in obtaining access to an internal body organ of a patient comprises, in accordance with the present invention, the steps of (a) providing a needle with a longitudinally extending passage and a dilating component disposed in the passage, the dilating component including an elongate rigid member and a stretchable membrane connected to one another to define an elongate transversely expandable channel, (b) inserting the needle with the dilating component into the internal body organ, (c) withdrawing the needle while leaving the dilating component in the internal body organ, and (d) expanding the dilating component to facilitate access to the internal body organ.

Pursuant to another feature of the present invention, the step of expanding the dilating component includes the step of inserting a plurality or progressively thicker dilating members into the dilating component, thereby progressively stretching the membrane portion.

According to a further feature of the present invention, the method additionally comprises the steps of inserting an endoscope through the expanded dilating component and using the endoscope to visualize body tissues internal to the internal body organ.

Another method for use in obtaining access to an internal body organ of a patient comprises, in accordance with the present invention, the steps of (i) providing a dilating component including an elongate rigid member and a stretchable membrane connected to one another to define a transversely expandable elongate channel, a needle being disposed in the channel, (ii) inserting the needle with the dilating component into the internal body organ, (iii) withdrawing the needle while leaving the dilating component in the internal body organ, and (iv) expanding the dilating component to facilitate access to the internal body organ.

Yet another method for use in obtaining access to an internal body organ of a patient comprises, in accordance with the present invention, the steps of puncturing the internal body organ with a hollow needle having a longitudinally extending passage and inserting through the passage a dilating device having an elongate substantially rigid member and a stretchable membrane connected thereto to define an elongate transversely expandable channel. Subsequently, the needle is removed from the internal body organ and from about the dilating device, while the dilating device is maintained in the internal body organ Then, the dilating component is expanded to facilitate access to the internal body organ.

This method may further comprise the steps of inserting a catheter at least partially through the dilating device and partially into the internal body organ and, upon a partial insertion of the catheter into the internal body organ, removing the dilating device from the internal body organ and from around the catheter. In this case, the internal body organ may be a blood vessel.

In this method, the step of inserting the dilating device through the needle may be performed prior to or subsequently to the step of puncturing the organ with the needle.

A device and associated method in accordance with the present invention facilitate access to a patient's organs. Access is obtaining while minimizing trauma to the organs. In many cases, the organs are not torn or cut in the process of inserting or disposing a catheter or endoscopic instrument.

A device and associated method in accordance with the present invention enable the performance of diagnostic investigations and surgical operations on organs or parts of organs which are hidden and would otherwise require significant incising of the patient's internal body tissues. Generally, this method decreases average hospitalization time and lowers costs.

A method for inserting a relatively large catheter into a vein, in accordance with the present invention, has fewer steps than the conventional wire-facilitated technique. Accordingly, a method in accordance with the present invention is faster and easier than the prior technique.

Use of a device in accordance with the present invention reduces the incidence of torn veins. The effectiveness of the device also saves time in that catheterization procedures need not be repeated as when veins are torn.

A device in accordance with the present invention is easy and inexpensive to manufacture.

BRIEF DESCRIPTION OF THE DRAWING

FIG. 4 is a schematic side perspective view of a dilating device for use in a method in accordance with the present invention.

FIG. 5 is a schematic side perspective view of an assembly for use in obtaining access to an internal organ of a patient, in accordance with the present invention, showing a dilating device in a collapsed configuration.

FIG. 6 is a partial schematic side perspective view of the dilating device of FIG. 5, showing the device in a partially expanded configuration.

FIG. 7 is a schematic side perspective view of a further dilating device for use in a method in accordance with the present invention.

FIG. 9 is a schematic side perspective view of two internal organs of a patient, showing utilization of the dilating device of FIG. 4 to obtain access to one organ through another organ, in accordance with the present invention.

DETAILED DESCRIPTION

Figure 1:
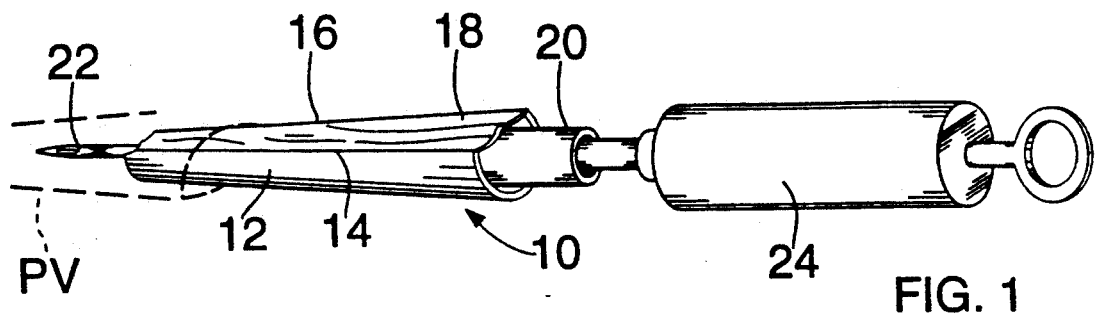
FIG. 1 is a schematic side perspective view of a catheterization assembly in accordance with the present invention.

As illustrated in FIG. 1, an assembly for use in obtaining intravenous or intra-arterial access comprises a dilating device 10 including an elongate solid body portion or rigid member 12 in the form of a cylindrical or conical segment having a pair of longitudinally extending edges 14 and 16. Vein dilating device 10 also includes an elastic membrane 18 connected to body portion 12 along edges 14 and 16.

The intravenous or intra-arterial catheterization assembly of FIG. 1 further comprises a relatively large diameter catheter 20 inserted into dilating device or sheath 10. A needle 22 is inserted through catheter 20 and is connected at a proximal end to a hypodermic syringe 24, e.g., for obtaining a blood sample to determine proper intravenous placement.

Membrane 18 provides dilating device 10 with a variable transverse cross-section, whereby the dilating device can be inserted at a relatively small diameter into a patient's vein PV and can expand to facilitate insertion of catheter 20 into vein PV. Dilating device 10 thus facilitates the feeding of intravenous fluid at a relatively large rate into vein VV.

In a method which utilizes the intravenous catheterization assembly of FIG. 1 for assisting in the deployment of intravenous or intra-arterial catheter 20, blood vessel or vein PV is first pierced or punctured by needle 22. Dilating device 10 is then slid over needle 22 into vein PV. Subsequently, catheter 20 is inserted at least partially through dilating device 10 and partially into vein PV. Upon a partial insertion of catheter 20 into vein PV, dilating device 10 is removed from vein PV and from around catheter 20. Simultaneously, needle 22 is extracted from catheter 20.

Figure 2:
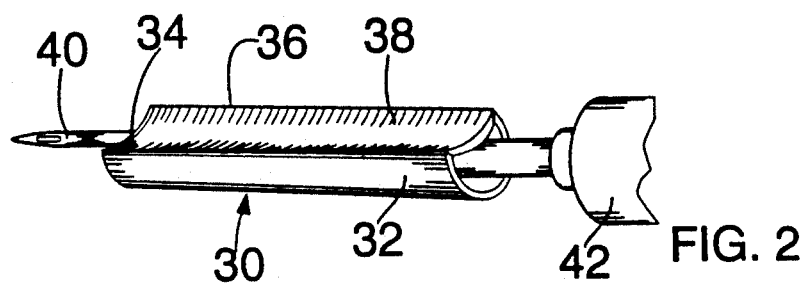
FIG. 2 is a schematic side perspective view of another catheterization assembly in accordance with the present invention.

As illustrated in FIG. 2, another assembly for use in obtaining intravenous or intra-arterial access comprises a dilating device 30 including an elongate rigid member or solid body portion 32 in the form of a cylindrical segment or shell having a pair of longitudinally extending edges 34 and 36. Vein dilating device 30 also includes an elastic membrane 38 connected to body portion 32 along edges 34 and 36.

The intravenous or intra-arterial catheterization assembly of FIG. 2 further comprises a needle 40 which longitudinally traverses dilating device 20. Needle 40 is coupled at a proximal end to a hypodermic syringe 42.

Membrane 38 provides dilating device 30 with a variable transverse cross-section, whereby the dilating device can be inserted at a relatively small diameter into a patient's vein VV (FIGS. 3A-3C) and can expand to facilitate insertion of a catheter 44 into vein VV. Dilating device 30 thus facilitates the feeding of intravenous fluid at a relatively large rate into vein VV.

Figure 3A:
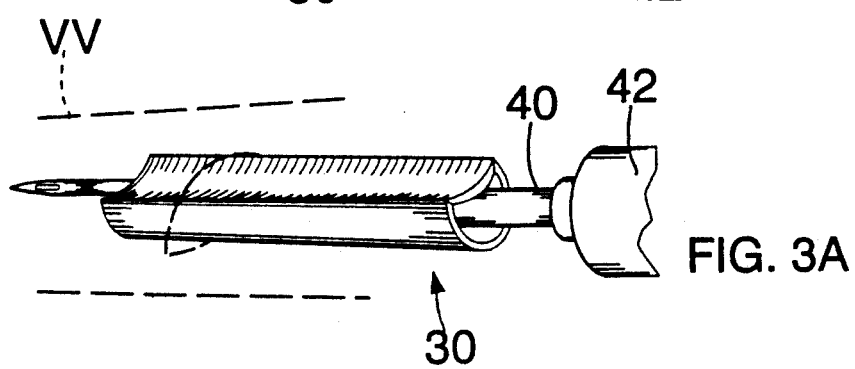
FIGS. 3A-3C are schematic side perspective views of a sequence of steps showing the utilization of the catheterization assembly of FIG. 2 in inserting an intravenous catheter into a vein.
Figure 3B:
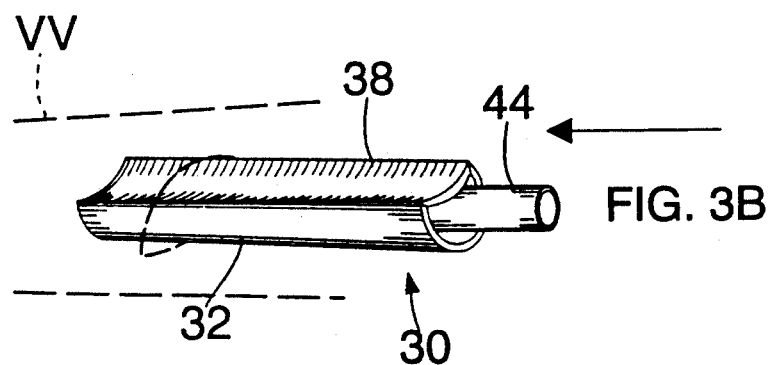
Figure 3C:
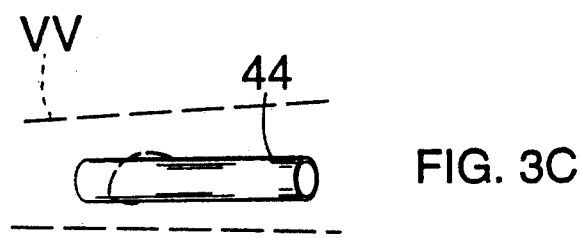

In a method which utilizes the intravenous catheterization assembly of FIG. 2 for assisting in the deployment of intravenous or intra-arterial catheter 44, blood vessel or vein VV is first pierced or punctured by needle 40. Dilating device 30 is then slid over needle 40 into vein VV, as illustrated in FIG. 3A. Subsequently, needle 40 is removed from dilating device 30 and replaced by relatively large diameter catheter 44, as depicted in FIG. 3B. Catheter 44 is inserted at least partially through dilating device 30 and partially into vein VV. Upon a partial insertion of catheter 44 into vein VV, dilating device 30 is removed from vein VV and from around catheter 44 (FIG. 3C).

It is to be noted that intravenous facilitation or vein dilating devices 10 and 30 may alternatively function as catheters designed to remain in vein PV or VV. In that case, the proximal end of the dilating devices 10 and 30 may be provided with coupling elements (not shown) for facilitating the attachment of the dilating devices to intravenous feed tubes.

As illustrated in FIG. 4, another expandable catheter or dilating device 48 for use in a catheter insertion or installation procedure as described hereinabove with reference to FIGS. 1-3C comprises a pair of elongate rigid members 50 and 52 in the form of cylindrical or conical segments each having a pair of longitudinally extending edges 50a, 50b and 52a, 52b. A first elastic membrane section 54 is attached to cylindrical segments 50 and 52 along edges 50a and 52a, while a second elastic membrane section 56 is connected to segments 50 and 52 along edges 52a and 52b, respectively. Membrane sections 54 and 56, together with segments 50 and 52, define an elongate transversely expandable channel through which a needle 22 and catheter 20 may be inserted, as described above with reference to FIG. 1.

Dilating device 48 may also be used in facilitating endoscopic inspection and endoscopic operating procedures, as described hereinafter with reference to FIGS. 8A-8D and 9. Dilating device 48 is of substantially larger dimensions, of course, when used in such a technique, than when used as an expandable venous catheter or in a catheter insertion procedure, as detailed above.

As illustrated in FIGS. 5 and 6, an alternative assembly for enabling or facilitating venous access comprises a hollow needle 60 with a longitudinally extending passage 62 and a dilating component 64 disposed in the passage. Dilating component 64 includes a pair of elongate rigid members 66 and 68 and a pair of elastic membranes 70 and 72 connecting longitudinally extending edges of the rigid members 66 and 68 to thereby define a longitudinally extending transversely expandable channel 74 (FIG. 6).

In using the access facilitating assembly of FIG. 5, dilating component 64 is first inserted into passage 62 of needle 60. This insertion step may be performed as part of a manufacturing and packaging process. In that case, needle 60 is sold prepackaged with dilating component 64 inserted therein. Of course, the access facilitating assembly is sterilized prior to disposition in a packaging container. Similarly, the catheterization assembly of FIG. 1 or 2 may also be sold as a prepackaged sterilized combination.

Upon a removal of needle 60 and dilating component 64 from their package, the sharp distal tip 76 of needle 60 is inserted into a selected internal organ, for example, a vein. Distal tip 76 is formed so as to permit a removal of needle 60 from the vein, while maintaining the distal end of dilating component 64 inside the vein. To that end, dilating component 64 is longer than needle 60 to enable a retaining force to be applied to the dilating component while a withdrawal force is exerted on needle 60.

Upon the removal of needle 60 from the selected vein, a catheter (not shown) may be inserted through dilating component 64 into the vein. Additionally, prior to the insertion of the catheter, dilating device 64 may be gradually expanded by the insertion of a dilating rod (not illustrated). In addition, a succession of ever larger rods may be inserted into dilating component to gradually increase the transverse dimension thereof.

FIG. 6 shows dilating component 64 in a partially expanded configuration.

As depicted in FIG. 7, a dilating device 78 for use in obtaining access to a vein or other internal organ of a patient in a method as described herein comprises an integral elastic or flexible web 80 having an elongate cylindrical form in an expanded configuration. Attached to web 80 along an outer (or inner) surface thereof are several elongate reinforcement ribs 82 of a substantially rigid material. Ribs 82 enable web 80 to maintain an elongate, substantially linear configuration during use of dilating device 78.

Dilating device 78 may be used in any of the access facilitating assemblies described herein. More specifically, dilating device 78 may be inserted inside a needle or may be inserted into a vein or other organ while surrounding a needle.

As illustrated in FIGS. 8A-8D, an endoscopic or laparoscopic technique utilizing a dilating device 48 (or 78) for inspecting or operating on internal tissues comprises an initial step of inserting a needle 84 through the dilating device 48 and then inserting the distal end of the needle and the dilating device into a selected organ OS. If the technique is being used, for example, to make a visual inspection or to obtain a biopsy from a site SS inside organ OS, the site has been previously located by another technique, for example, by a CAT scan or NMR imaging procedure.

In the event that the operation is laparoscopic, needle 84 and dilating device 48 is inserted into the patient through a trocar sleeve or laparoscopic cannula 86.

Figure 8A:
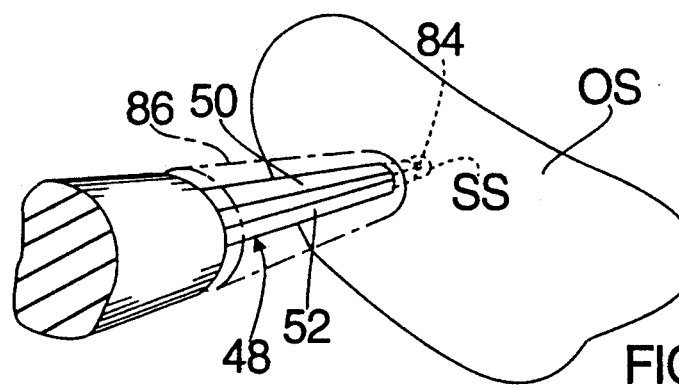
FIGS. 8A-8D are schematic side perspective views of a sequence of steps showing the utilization of a dilating device in accordance with the present invention, for facilitating the obtaining of diagnostic and surgical access to an internal organ of a patient.
Figure 8B:
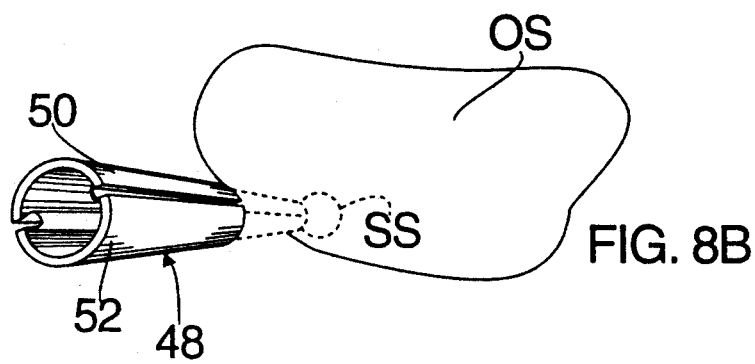
Figure 8C:
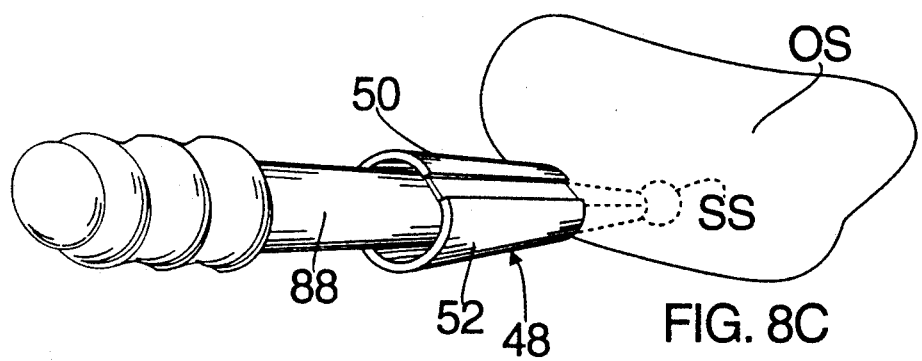
Figure 8D:
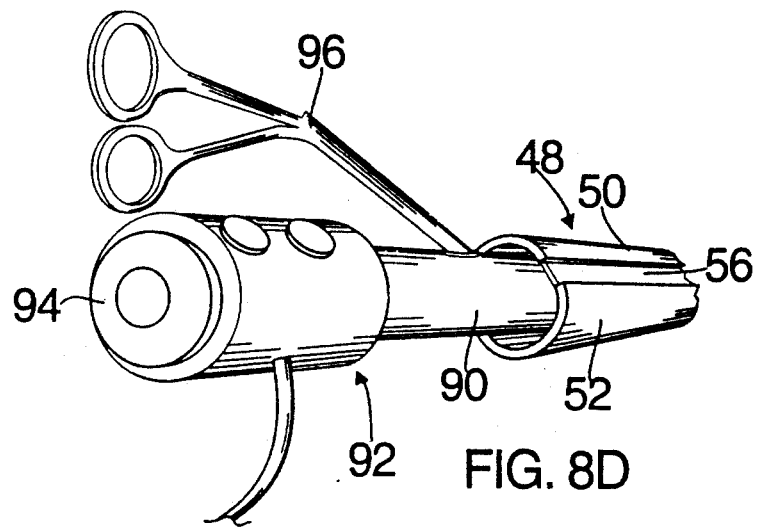

Upon the insertion of needle 84 a predetermined distance into the organ OS, needle 84 is removed while maintaining the distal end portion of dilating device 48 inside the organ, as illustrated in FIG. 8B. Subsequently, as shown in FIG. 8C, an expander rod 88 is inserted through dilating device 48. Preferably, a series of expander rods 88 of gradually increasing thickness are successively inserted into dilating device 48, thereby increasing the size of a passage through organ OS without tearing or cutting the tissues of the organ.

Upon a sufficient expansion of dilating device 48, an insertion member 90 of an endoscope or laparoscope 92, schematically illustrated in the drawing, is inserted through the expanded or dilated dilating device 48. The operator then views the internal tissues of organ OS via an eyepiece 94 of endoscope or laparoscope 92. In addition, a biopsy forceps 96 may be inserted through a biopsy channel 96 in insertion member 90 to obtain a sample of the tissues at site SS.

As illustrated in FIG. 9, the procedure described above with reference to FIGS. 8A-8D may be used to inspect a second organ such as the gall bladder GB through a first organ such as the liver LO. In that case, dilating device 48 (or 78) is inserted entirely though the liver LO, to the surface of the gall bladder GB.

Although the invention has been described in terms of particular embodiments and applications, one of ordinary skill in the art, in light of this teaching, can generate additional embodiments and modifications without departing from the spirit of or exceeding the scope of the claimed invention. For example, a procedure as described hereinabove with reference to FIGS. 8A-8D may be used to perform operations endoscopically. The procedure may be used in other kinds of surgery such as thryoid surgery or neurosurgery.

Accordingly, it is to be understood that the drawings and descriptions herein are profferred by way of example to facilitate comprehension of the invention and should not be construed to limit the scope thereof.

What is claimed is:

1. A method for use in obtaining access to an internal body organ of a patient, comprising the steps of:
    providing a dilating component including an elongate rigid member and a stretchable membrane connected to one another to define a transversely expandable elongate channel, an elongate auxiliary member having a sharp distal end being disposed in said channel;
    inserting said auxiliary member with said dilating component into the internal body organ;
    withdrawing the auxiliary member while leaving said dilating component in the internal body organ;
    upon withdrawal of said auxiliary member from said dilating component, inserting an elongate dilating member at least partially through said dilating component; and
    stretching said membrane and concomitantly expanding said dilating component as a consequence of said step of inserting said dilating member, to facilitate access to the internal body organ.

2. The method defined in claim 1 wherein said dilating member is one of a series of progressively thicker dilating members inserted into said dilating component, thereby progressively stretching said membrane.

3. The method defined in claim 1, further comprising the steps of inserting an endoscope through the expanded dilating component and using said endoscope to visualize body tissues internal to the internal body organ.

4. A method for using in obtaining access to an internal body organ of a patient, comprising the steps of:
    providing a needle with a longitudinally extending passage and a dilating component disposed in said passage, said dilating component including an elongate rigid member and a substantially stretchable membrane connected to one another to define an elongate transversely expandable channel;
    inserting said needle with said dilating component into the internal body organ;
    withdrawing the needle while leaving said dilating component in the internal body organ;
    upon withdrawal of said needle from about said dilating component, inserting an elongate dilating member at least partially through said dilating component; and
    stretching said membrane and concomitantly expanding said dilating component as a consequence of said step of inserting said dilating member, to facilitate access to the internal body organ.

5. The method defined in claim 4 wherein said dilating member is one of a series of progressively thicker dilating members inserted into said dilating component, thereby progressively stretching said membrane.

6. The method defined in claim 4, further comprising the steps of inserting an endoscope through the expanded dilating component and using said endoscope to visualize body tissues internal to the internal body organ.

7. A method for use in obtaining access to an internal body organ of a patient, comprising the steps of:
    puncturing the internal body organ with a hollow needle having a longitudinally extending passage;
    inserting through said passage a dilating device having an elongate substantially rigid member and a stretchable membrane connected thereto to define an elongate transversely expandable channel;
    removing said needle from the internal body organ and from about dilating device, while maintaining said dilating device in the internal body organ;
    upon withdrawal of said auxiliary member from said dilating component, inserting an elongate dilating member at least partially through said dilating component; and
    stretching said membrane and concomitantly expanding said dilating component as a consequence of said step of inserting said dilating member, to facilitate access to the internal body organ.

8. The method defined in claim 7 wherein said dilating member is one of a series of progressively thicker dilating members inserted into said dilating component, thereby progressively stretching said membrane.

9. The method defined in claim 7, further comprising the steps of inserting an endoscope through the expanded dilating component and using said endoscope to visualize body tissues internal to the internal body organ.

10. The method defined in claim 7, further comprising the steps of:

inserting a catheter at least partially through said dilating device and partially into the internal body organ; and upon a partial insertion of said catheter into the internal body organ, removing the dilating device from the internal body organ and from around said catheter.

11. The method defined in claim 7 wherein the internal body organ is a blood vessel.

12. The method defined in claim 7 wherein said step of inserting is performed prior to said step of puncturing.

13. The method defined in claim 7 wherein said step of inserting is performed subsequently to said step of puncturing.

* * * * *